United States Patent
Riedel et al.

(10) Patent No.: US 9,474,697 B2
(45) Date of Patent: Oct. 25, 2016

(54) DENTAL ELASTOMERIC IMPRESSION MATERIAL WITH HIGH VISCOSITY, DIMENSIONAL STABILITY AND STORAGE DURABILITY

(75) Inventors: Norman Hendrik Riedel, Frankfurt am Main (DE); Wigand Krumme, Cuxhaven (DE); Tobias Blömker, Cuxhaven (DE); Manfred Thomas Plaumann, Cuxhaven (DE)

(73) Assignee: VOCO GmbH, Cuxhaven (DE)

( * ) Notice: Subject to any disclaimer, the term of this patent is extended or adjusted under 35 U.S.C. 154(b) by 642 days.

(21) Appl. No.: 13/409,886

(22) Filed: Mar. 1, 2012

(65) Prior Publication Data

US 2013/0101954 A1 Apr. 25, 2013

(30) Foreign Application Priority Data

Mar. 1, 2011 (DE) .................. 10 2011 012 745

(51) Int. Cl.
*A61K 6/10* (2006.01)
*A61C 9/00* (2006.01)

(52) U.S. Cl.
CPC ............... *A61K 6/10* (2013.01); *A61C 9/0006* (2013.01)

(58) Field of Classification Search
CPC ....................................................... A61K 6/10
See application file for complete search history.

(56) References Cited

U.S. PATENT DOCUMENTS

| | | | |
|---|---|---|---|
| 3,445,420 A | 5/1969 | Kookootsedes et al. | |
| 3,715,334 A | 2/1973 | Karstedt | |
| 3,775,352 A | 11/1973 | Leonard, Jr. | |
| 3,814,730 A | 6/1974 | Karstedt | |
| 3,933,880 A | 1/1976 | Bergstrom et al. | |
| 3,989,667 A | 11/1976 | Lee et al. | |
| 4,879,339 A | 11/1989 | Yoshino et al. | |
| 5,066,714 A | 11/1991 | Inoue et al. | |
| 6,013,711 A * | 1/2000 | Lewis .................. | A61K 6/083 524/265 |
| 6,552,104 B1 | 4/2003 | Hare | |
| 8,278,367 B2 * | 10/2012 | Boettcher et al. ........... | 523/109 |
| 2004/0110863 A1 | 6/2004 | Zech et al. | |

FOREIGN PATENT DOCUMENTS

| | | |
|---|---|---|
| EP | 0 152 887 A2 | 8/1985 |
| EP | 0 158 141 A2 | 10/1985 |
| EP | 0 166 107 A2 | 1/1986 |
| EP | 0 219 660 A2 | 4/1987 |
| WO | 99/62461 A1 | 12/1999 |
| WO | 02/078647 A1 | 10/2002 |
| WO | WO 2008059468 A2 * | 5/2008 |

* cited by examiner

*Primary Examiner* — Michael Pepitone
(74) *Attorney, Agent, or Firm* — Vidas, Arrett & Steinkraus, P.A.

(57) ABSTRACT

The invention relates to a two-component dental elastomeric impression material with dimensional stability and storage durability based on addition curing silicone, wherein one component comprises a polymerization catalyst, containing or composed of a) at least one polydimethylsiloxane comprising polyatomic cross-linkable groups, preferably unsaturated cross-linkable groups,
b) at least one polyaklysiloxane with Si—H functionalities,
c) at least one catalyst for the reaction of a polydimethysiloxane, comprising polyatomic cross-linkable groups, with a polydimethylsiloxane comprising Si—H functionalities
d) one or more fillers,
e) a combination of release agents, comprising
i) at least one alkyl-substituted polydimethylsiloxane, in which the alkyl chain is linear or branched, and/or at least a polydimethylsiloxane, in which the alkyl chain is linear or branched, and partially or completely halogenated, preferably fluorinated, and
ii) at least one paraffin, and further relates to a dental mold, use, a dental kit, and a production method relating respectively to the dental impression mass.

15 Claims, 7 Drawing Sheets

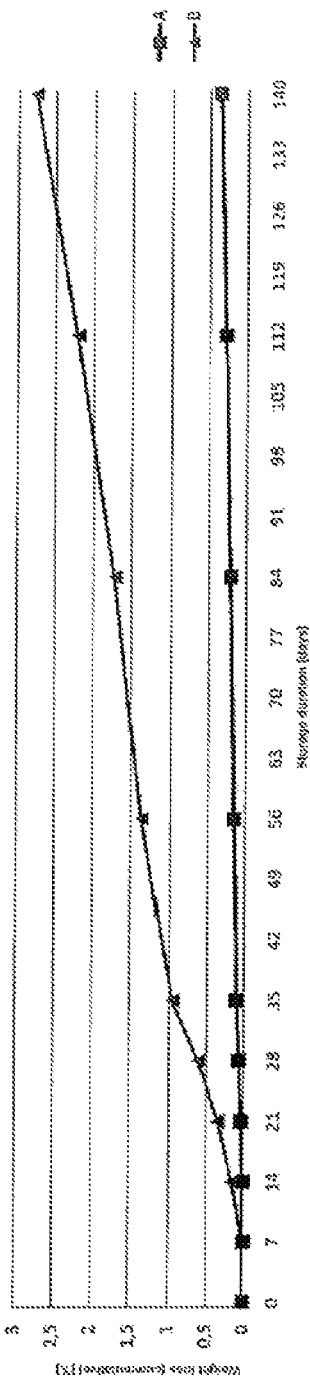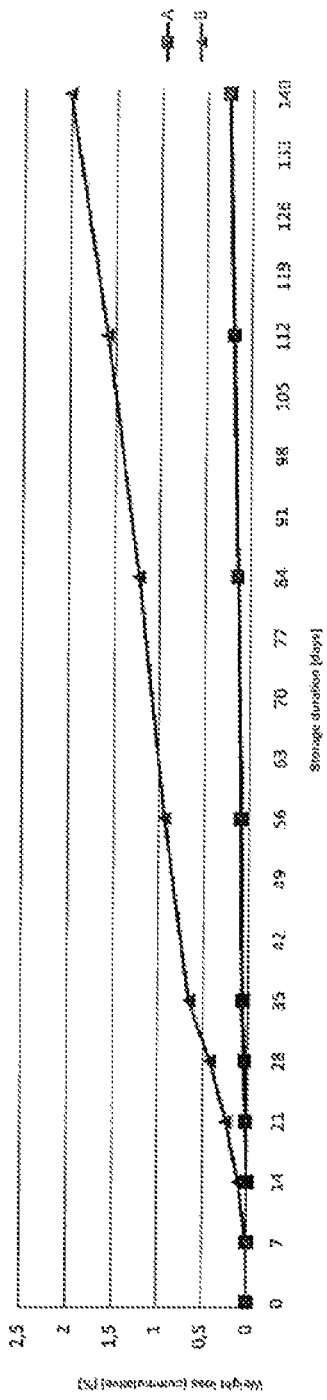

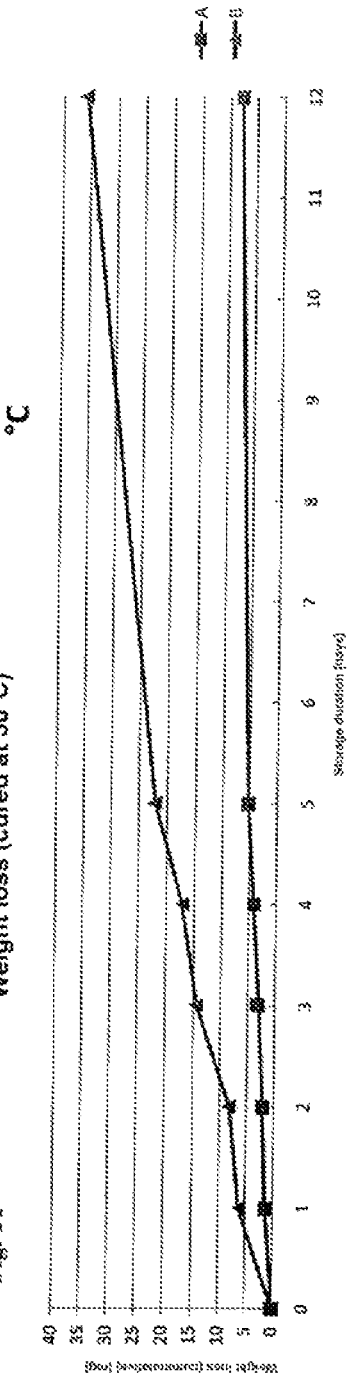
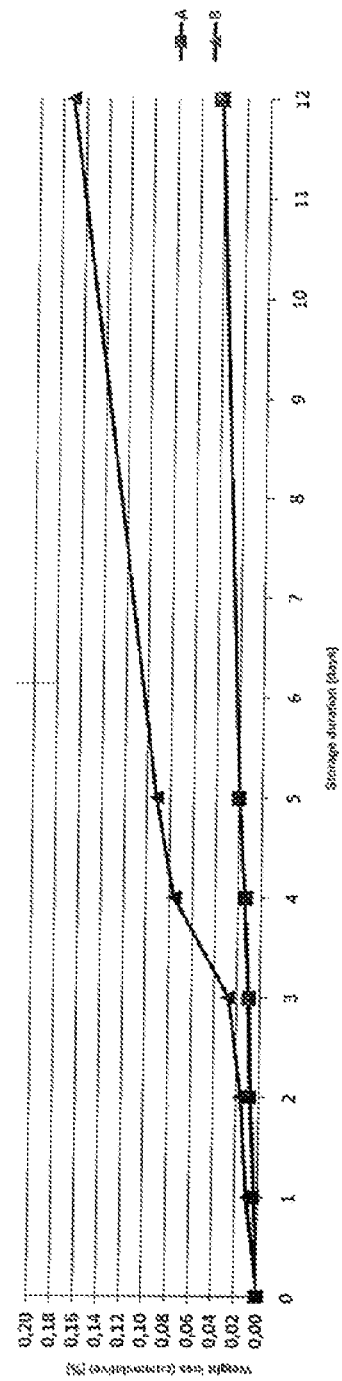

DENTAL ELASTOMERIC IMPRESSION MATERIAL WITH HIGH VISCOSITY, DIMENSIONAL STABILITY AND STORAGE DURABILITY

CROSS-REFERENCE TO RELATED APPLICATIONS

Not applicable.

STATEMENT REGARDING FEDERALLY SPONSORED RESEARCH

Not applicable.

BACKGROUND OF THE INVENTION

The present invention relates to a dental elastomeric impression material of high, or respectively very high, consistency, whose consistency test disk according to ISO 4823 has a maximum diameter of 35 mm.

The consistency test according to the ISO standard is a measurement using two glass plates, wherein 0.5 ml of the elastomer to be tested is applied on the base disc and subsequently, using a second plate, is pressed under the influence of a prescribed force. The consistency is classified into different types based on the average diameter of the resulting disc.

The present invention relates to preferred materials of the type class 0, that is high viscosity or kneadable materials, also called putty mass or putties.

During dental impressions, the impression material is introduced into the oral cavity in a plastic state, where it undergoes a phase change and transitions into a firm elastic or rigid state, so that it is possible to remove the mold from the oral cavity in a fixed form and without changes to the form thereof.

Thus, the present invention relates to dental putty based on addition curing silicone. This substance class which deals with cold curing two-component systems, in which two pastes are mixed together that cure with each other after a few minutes at room temperature, is characterized by an extremely low shrinkage during the curing, and generally reproduces the situation to be modeled in the patient in a dimensionally accurate and exactly detailed manner.

Dental putty masses based on addition curing silicone are frequently used in a so-called correction impression. For this purpose, a first impression (pre-impression) of the heavy flowing or kneadable elastic silicone material is performed in the tray.

While producing the pre-impression, it is desirable that the impression material is stable, and thus the insertion of the impression tray filled with putty into the patient's mouth meets resistance. The insertion of the tray is slowed by the resistance, whereby depressing the tray up to the dental surface can be avoided. Contact of the bottom of the tray and the dental surfaces is painful for the patient and leads to an incorrect shape, because there is no longer any impression material present on the contact surfaces.

After removal of the impression from the mouth, the mold is trimmed for removing undercuts and for creating outflow possibilities for the thin flowing silicone material during the second impression (correction impression). The pre-impression is corrected with the second impression in order to increase the detail resolution of the first mold in the cervical and subgingival region. For this purpose, the tooth arch of the first mold is filled in the tray with a low viscosity material of the same chemical nature. If necessary, the prepared tooth is additionally overmolded. By reinserting the tray, the correction material is displaced up to a thin correction layer. It binds with the polymerized first material, and cures as well. During the penetration of the tooth/tooth stump into the hollow space of the first impression filled with the low viscosity material, sufficient pressure is generated to guarantee that the material is also pressed into regions that are difficult to reach, such that even the smallest details of the preparation are precisely reproduced.

The correction impression described above is also called a two-step two-phase impression, because the method is performed successively using two materials of different viscosities with the same chemical basis.

In addition, dental putty masses based on addition curing silicone are also frequently used in a so-called double mix impression. For this purpose, the prepared tooth in the mouth of the patient is overmolded using a low viscosity impression material. While the material is still flowable, the tray with the putty is now placed in the mouth. Both material phases then harden together into a mold.

The double mix impression is also called a one-step two-phase impression, because with this method the tray is filled with the putty and at the same time, the tooth/tooth stump is overmolded with the low viscosity silicone.

BRIEF SUMMARY OF THE INVENTION

The present invention relates further to compositions for producing dental putty masses, and methods for producing dental molds using putties according to the invention, and it also relates to the dental molds themselves that can be produced by curing the putty according to the invention. The subject matter of the invention is also a kit for producing dental molds, comprising the putty according to the invention. Finally, the invention relates to the use of a putty according to the invention for producing dental molds.

For use, the two pastes are removed from their storage containers using metering spoons, and the portions, that are as equal in size as possible, are kneaded together by hand into a homogeneous mass. This mass is placed into an impression tray and used according to the method described above. The mass hardens within a few minutes, and can then be removed from the patient's mouth. The mold is then produced from the polymer.

When removing the paste from the storage containers, and while mixing the paste by kneading using the fingers, it is important that the mass does not adhere to the removal spoons, or respectively to the fingers, or leave a residue. This can be attained to a certain degree by adding suitable fillers and/or inert additives in the form of hydrocarbons, for example paraffin oils, in an exactly adjusted quantity. However, a problem has been observed with these putty compositions, in that with such composite pastes large portions of the hydrocarbons that are free and not chemically bound in the compositions, escape from the mass and are released both during storage as well as after curing. This phenomenon is also designated as sweating because in the process droplets of the additive form on the surface of the two pastes, or later also on the surface of the impression.

The sweating of the additives, which initially make the putty mass kneadable and easily workable, can have a crucial impact on the quality of the impression:

The hydrocarbons that migrate to the surface and precipitate out of the compound of the silicone network can seriously disrupt, or even completely prevent, the adhesion between the cured putty mass and the low viscosity correction material. Furthermore, the adhesion of the putty mass to the walls of the impression tray can be reduced due to the sweating such that a clear and precisely detailed impression cannot be achieved.

There have been a few attempts in the prior art to solve the problem cited above and to disclose easily kneadable putty masses that do not release and sweat their additives.

The patent EP 0 152 887 B1, the entire contents of which is incorporated herein by reference, entitled "Modified fillers for silicone pastes, their use and dental impressions containing them", discloses the use of paraffin-laden fillers in the pastes. In order to eliminate the tackiness in the pastes, preferably only approximately 4-5% by weight of paraffin oil should be required in the paste, of which however approximately 1-2% by weight paraffin oil is already found on the surface of the filler. Accordingly, the pastes should contain only approximately 2-4% by weight of free paraffin oil, which in turn, has an affinity to the paraffin oil-laden filler and should be less inclined to sweat. Putties, or respectively impressions, that are storage durable should be obtained in this manner. Hardly any droplets of paraffin oil should form in the pastes, or respectively on the impressions.

The document, EP 0 166 107 A2, the entire contents of which is incorporated herein by reference, entitled "Use of paraffin or microcrystalline waxes for silicone pastes, their manufacture and application" states that the named problems can be avoided by using paraffin or microcrystalline waxes in the pastes. In order to eliminate the tackiness in the pastes, preferably only approximately 4-5% by weight of paraffin oil and 1.5-5% by weight paraffin or microcrystalline wax should be required in the pastes. The waxes are solid at room temperature because they have a melting range between 30-55° C. They are incorporated into the mass by the energy supplied by kneading during the production of the pastes. The paraffin oil in these pastes should be less inclined to sweat, and putties, or respectively, impressions, that are storage durable should be obtained in this manner. Hardly any droplets of paraffin oil should form in the pastes, or respectively on the impressions.

The document EP 0 158 141 B1, the entire contents of which is incorporated herein by reference, ("Pastes containing platinum, organopolysiloxanes and fillers") describes dental pre-impression masses that can be mixed particularly quickly and easily and that leave no, or practically no traces, when the pastes are mixed by kneading with bare hands. The catalyst paste contains 10 to 25% by weight of hydrocarbons that are liquid or spreadable at room temperature and free of aliphatic C—C multiple bonds. Paraffin oils and petroleum are preferably used. The sweating of the hydrocarbons was not tested.

The document, EP 0 219 660 B1, the entire contents of which is incorporated herein by reference, entitled "Polysiloxane compositions for taking dental impressions" refers to the publications referenced above, and explains that it was already disclosed in these documents that putty containing n-paraffins reduce the tackiness of the mass to the hands of the person processing it. However, such pastes as well as the impressions produced therefrom will sweat part of the paraffin during storage, whereby impressions do not maintain sufficient precision.

The patent specification further explains that with efforts to further improve the putty masses it was found that modifications to the mass with isoparaffins with 8-24 C atoms leads to high value putties. The masses are distinguished by the storage durability thereof and lubricating effect during mixing of the base and catalyst pastes. The masses should be suitable for producing exact impressions, specifically also impressions of teeth. The isoparaffins isohexadecane and isoeicosane are preferably used.

The inert hydrocarbons that are added to the dental putty masses as additives for reducing the tackiness when mixing the two components by hand, are also designated as a release agent or plasticizer. The effectiveness of the addition thereof to the dental mass relates not only to a simple and non-adhesive kneading of the two components by hand. The non-adhesive consistency also leads to the fact that the mixed material can be still be manipulated in the impression tray, for example in order to move a larger quantity of paste to a desired location.

Furthermore, the additives confer to the pastes a particular malleability that simplifies, that is accelerates, mixing the two components together.

The "putty problem" cited above is taken up again in the document U.S. Pat. No. 4,879,339, the entire contents of which is incorporated herein by reference, ("Storage stable and room temperature curable organopolysiloxane composition"). It is stated therein that for reducing the tackiness typically liquid to semi-solid aliphatic hydrocarbons are added as a release agent to the kneadable and stable dental impression mass. Liquid paraffins and petrolatum are named as examples.

Hydrocarbons in the presence of the platinum catalyst, however, are susceptible to catalytic oxidation, whereby different oxidized groups, such as carboxylic acids, aldehyde or hydroperoxide, could be formed which for their part could at least partially deactivate and degrade the platinum catalyst. This in turn could lead to a delayed hardening or to a portion of monomers in the polymer that do not cure.

Accordingly, the patent specification proposes to add antioxidants to the putty mass in a quantity of at least 10 ppm, so that the release agent will not oxidize and therefore should retain its effectiveness for reducing the tackiness.

The patent, U.S. Pat. No. 5,066,714, the entire contents of which is incorporated herein by reference, entitled "Curable organopolysiloxane putty-like composition" distinguishes the behavior of the putty mass provided with internal release agents before and after curing. Due to intentional sweating before the polymerization, the aliphatic hydrocarbons ensure that the components of the putty mass do not adhere to the hands of the user of the mass; this fact represents a positive property of the mass, because practical handling of the mass is simplified due to this property; nevertheless, the addition of the release agent to the composition is detrimental to the dental mass because the release of the hydrocarbons gradually continues even after the hardening, and due to the discharge of the agent, the exact size of the hardened mold is distorted.

Therefore it is proposed in the patent specification to add as a release agent, instead of aliphatic hydrocarbons, an organopolysiloxane that has 5 to 50 mole % of alkyl groups with 7 to 30 carbon atoms, in a quantity of 5 to 60 percent by weight of the putty mass. Such a modification to the mass is intended to lead to the fact that the alkyl group-substituted polysiloxane in its function as a release agent, by releasing from the pastes, permits adhesive-free mixing of the components by hand, while the remainder of the release agent remains in the molding material after curing—in contrast to the formerly used aliphatic hydrocarbons.

The document WO 99/62461, the entire contents of which is incorporated herein by reference, entitled "Very high viscosity polysiloxane impression material" proposes putty impression materials that have an emulsifying plasticizer. The plasticizer is preferably an alkylphthalate, and particularly preferably an octylbenzylphthalate. The quantity of the plasticizer preferably amounts to 4-6% by weight of the entire composition. The plasticizer should improve the handling properties of the material, and in particular, reduce the tackiness of the putty mass during kneading the components by hand. The plasticizer should be emulsified by the presence of a wetting agent. This process should prevent the plasticizer from being released and sweated out of the polysiloxane matrix. Examples 7 and 8 of the document indicate that octylbenzylphthalate does not form any droplets on the surface of the mold material, and thus differs from the prior art.

The document U.S. Pat. No. 6,552,104 B1, the entire contents of which is incorporated herein by reference, entitled "Method of making hydophilic non-sweating polymerizable dental impression material", from the same applicant as the document WO 99/62461, elaborates on and explains the principle described in the WO document of a "plasticizer emulsified in the surfactant", in which both substances form a homogeneous phase.

As is generally known, sweating of the inert plasticizer results from the migration of the substance out of the molding material towards its surface, where the substance precipitates in the form of oily liquid droplets. The migration of the substance out of the network can lead to dissolving the material of an impression tray composed of polystyrene, and as already mentioned above, to a loss of mold accuracy.

The US document defines the term "sweating" as forming droplets of plasticizer on the outer surface of the hardened elastomeric mold material after 24 hours of storage at 23° C.

The term "non-sweating" means that the elastomeric mold material does not have any visible droplets (and/or a film) of plasticizer on the outer surface thereof in the hardened state after 24 hours of storage at 23° C.

The term "non-sweating" preferably means that the elastomeric mold material has less than 10% by weight of the plasticizer from the original putty composition in the form of visible droplets (and/or a film) on the outer surface thereof in the hardened state after 24 hours of storage at 23° C.

Particularly preferably, less than 5% by weight of the plasticizer from the original putty composition precipitates on the surface, and most particularly preferably less than 1% by weight.

The term "low liquid mass loss" means that elastomeric mold material undergoes less than 0.05% by weight loss after 12 days of storage at 23° C.

In this document, the phenomenon of sweating is also tested quantitatively for the first time on the hardened sample.

The use of alkyl phthalates must be viewed as a disadvantage of this inventive principle because many compounds of this chemical family have problems with respect to their toxicity, and by now compositions containing phthalate must be specifically labeled.

The document WO 02/078647 A1, the entire contents of which is incorporated herein by reference, (Silicone-based dental impression compounds) also relates to putty materials based on addition curing silicone, which in the mixed state has a non-tacky consistency, and which are suited for mixing by machine in conventional motor-driven mixing devices. A mechanized production and mixing of the paste represents an important technical advance in the use of dental putty masses because due to their high viscosity, they cannot be processed with common spatulas on mixing blocks, nor is it possible to use them in a double chamber cartridge with a static mixing tube.

It is proposed in the document to add 4-10% by weight of at least one paraffin oil or at least one white mineral oil or a mixture of at least one paraffin oil and at least one white mineral oil, to the putty mass as a plasticizer. As described above, the plasticizer obviously gives the paste not only "non-tackiness", but also a certain malleability in the rheological behavior thereof, that makes it possible to mix this stable and kneadable mass by machine.

With respect to this prior art, it was the primary object of the invention to specify a two-component dental elastomeric impression mass having high viscosity, dimensional stability and storage durability based on addition curing silicones, wherein the impression mass over the course of the life cycle thereof, starting from the production of the two pastes, the storage phase of the pastes, the course of the hardening thereof up to the cured polymer, has neither tackiness, nor a release, or respectively a sweating, of substances. Associated with this primary object for the specification of dental compositions for producing dental masses according to the invention, there were further objects, to specify corresponding molds according to the inventions, to propose corresponding kits for producing the molds according to the invention, and to disclose a method for using the mass according to the invention. According to the property profile according to the invention, the putty mass is to be usable for both kneading by hand as well as by machine using a conventional motor-driven automatic mixing device.

BRIEF DESCRIPTION OF THE SEVERAL VIEWS OF THE DRAWINGS

FIGS. 5 to 8 the cumulative weight loss of the individual pastes in percent by weight over time in days under different temperature conditions in a diagram;

FIGS. 9 to 11 the weight loss of the already hardened silicone formulation in mg over time under different temperature conditions in a diagram;

FIGS. 12 to 14 the weight loss of the already hardened silicone formulation in percent by weight over time in a diagram.

DETAILED DESCRIPTION OF THE INVENTION

Figure 1:
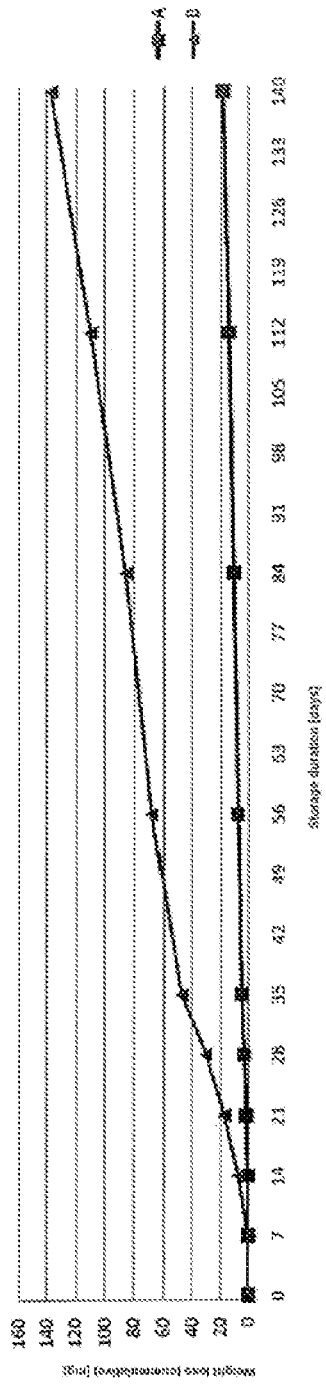
FIGS. 1 to 4 the cumulative weight loss of the individual pastes in mg over time in days under different temperature conditions in a diagram.
Figure 2:
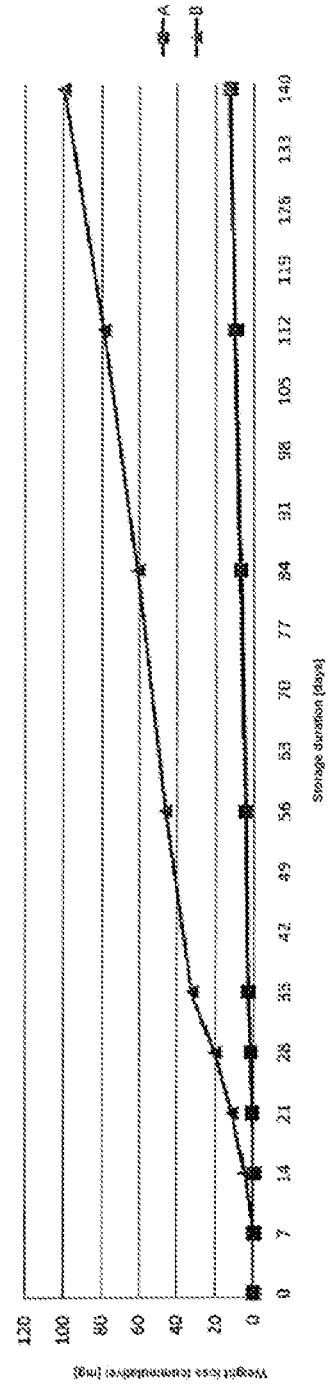
Figure 3:
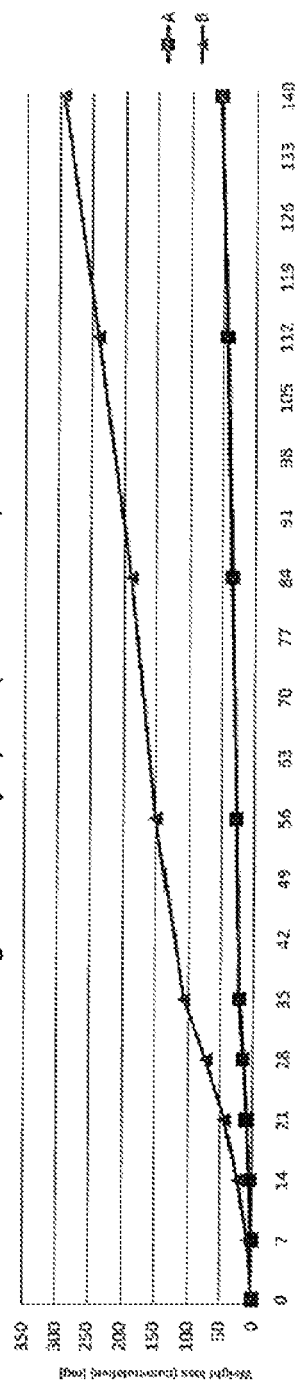
Figure 4:
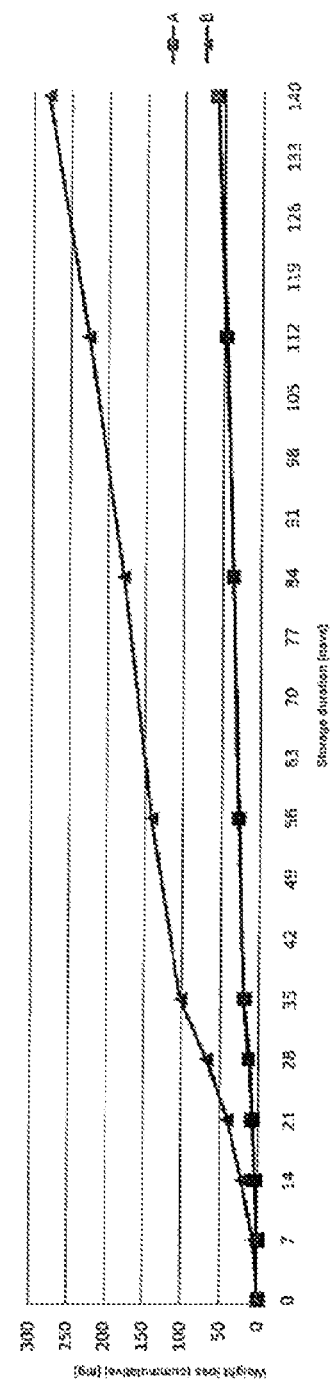
Figure 7:
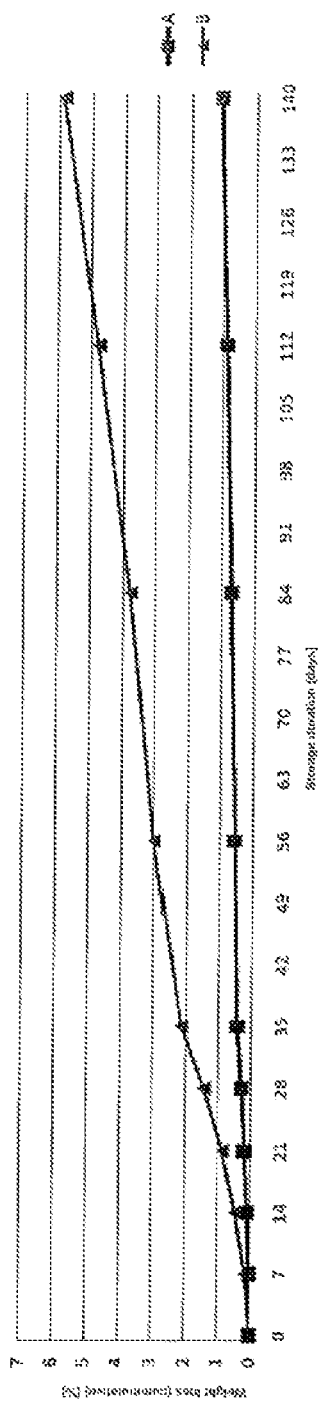
Figure 8:
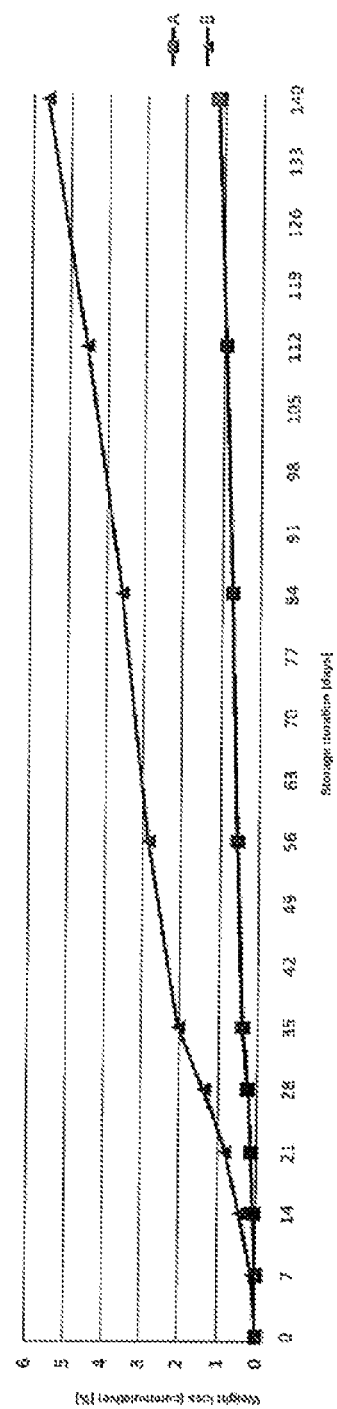
Figure 9:
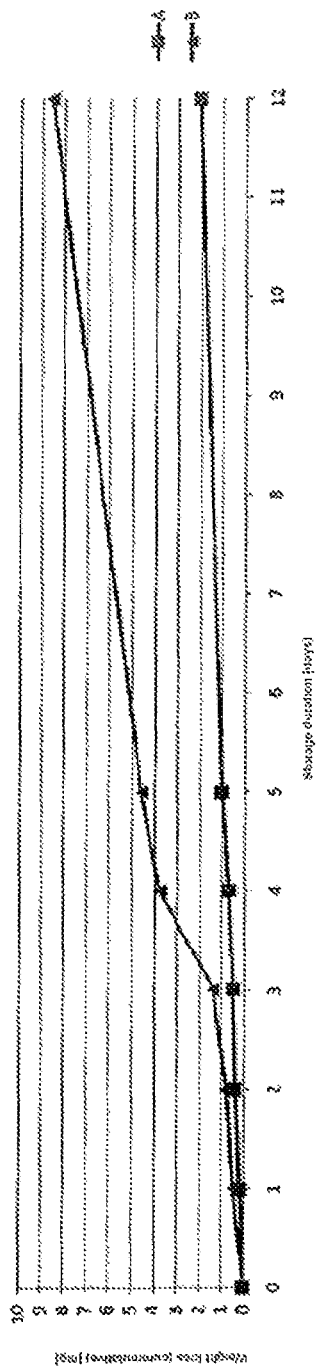
Figure 10:
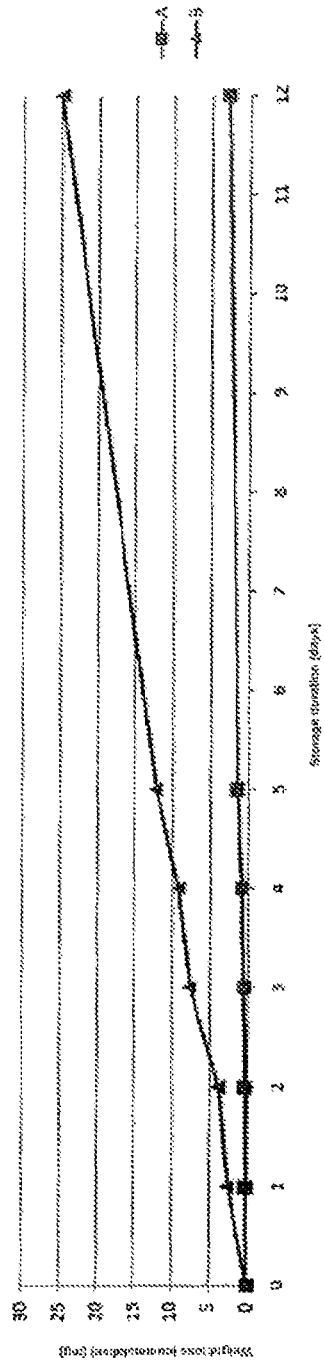

The base material according to the invention comprises the group of addition curing silicones. As they are cold hardening (that is, they harden at room temperature) and self-hardening systems, these addition curing silicones are particularly well suited for producing the putty masses according to the invention, because they have very low shrinkage during hardening. The hardening is a catalyzed addition reaction that occurs by hydrosilyation, a reaction of organohydrogen polysiloxanes (polysiloxane, that has organic groups, and Si—H bonds) to polysiloxane, comprising polyatomic cross-linkable groups, generally unsaturated cross-linkable groups, and preferably (possibly substituted) alkenyl groups, particularly vinyl groups or allyl groups.

The putty impression masses according to the invention based on addition curing silicones are formulated as two-component systems, and are composed of a so-called base paste and a catalyst paste. The base paste contains the polysiloxanes, comprising polyatomic cross-linkable groups, the organohydrogen polysiloxanes, filler, the combination of release agents and additives. The catalyst paste comprises a second portion of the polysiloxanes, comprising polyatomic cross-linkable groups, the catalyst for the cross-linking, and likewise, filler and further additives.

With the reaction, Si—C bonds are linked, wherein an Si—H bond is added to an C—C double bond. Thus, the chemistry of the hardening proceeds via the direct addition of an SiH function of the cross-linker to the unsaturated function of the polymer, forming a corresponding bridge, for example an ethylene bridge. Because such a mechanism does not provide a departing group or byproduct, addition curing silicone elastomers have no appreciable shrinkage caused by the polymerization.

The following is noted for the features of the invention a.) to e.):

For a.)

For the elasticity it is preferred that one or more of the siloxanes, comprising possibly substituted alkenyl groups is/are linear (that is, unbranched in the siloxane structure). In one such linear siloxane, there are two of the (possibly substituted) alkenyl groups per molecule, in particular vinyl groups or allyl groups disposed at the terminal ends of the chain.

Optionally, additional such groups are located in the middle of the chain (that is, not at the terminus) for increasing the degree of cross-linking, preferably, however, the number of these groups is not too high, for instance one or two groups per molecule, or even no additional such group in the middle of the chain, because the material loses the elastic properties thereof due to these groups, and becomes stiffer and more brittle.

The use of branched siloxanes comprising possibly substituted alkenyl groups is also optional.

Likewise, it is optional to use so-called VQM siloxanes (vinyl terminated quaternary modified siloxanes) in addition to linear siloxane. It is advantageous if these VQM siloxanes are composed of molecules with one silicon atom that is substituted with four siloxane chains, where the chains have a vinyl group located on each end. Such siloxanes advantageously benefit the hardness of the cured materials, without a great loss of flexibility or having to accept greater brittleness, thus they possibly represent an alternative to fillers which in many cases increase brittleness.

The use of linear vinyl-methyl polysiloxanes are particularly preferred. These have terminal dimethyl-vinyl siloxane units. Furthermore, it is particularly preferred to use a plurality of different polysiloxanes, in particular linear vinyl-methyl polysiloxanes of different viscosities. Thus, a mixture of two linear vinyl-methyl polysiloxanes is particularly preferred, wherein for example, one linear vinyl-methyl polysiloxane comprising terminal vinyl groups has a viscosity in the range of 1,000 mPa·s to 20,000 mPa·s, and a further linear vinyl-methyl polysiloxane comprising terminal vinyl groups has a viscosity in the range of 55,000 mPa·s to 120,000 mPa·s. The viscosity specification of the components relates to the dynamic viscosities which are measured according to DIN 53018 at 25° C.

The quantity of the linear vinyl-methyl polysiloxanes relative to the total quantity of the putty amounts to 1-40% by weight, preferably 5-30% by weight, and particularly preferred 10-25% by weight, wherein the weight ratio of the low viscosity siloxanes to the higher viscosity siloxanes is in the range of 5:1 to 1:5, preferably 3:1 to 1:3 and particularly preferably 1:1 to 1:3.

For b.)

The organohydrogen polysiloxanes are alkylhydrogen polysiloxanes (polysiloxanes that have both alkyl groups and Si—H bonds), wherein the alkyl groups preferably each have 1 to 4 C atoms and particularly preferably are methyl groups. Organohydrogen polysiloxanes with at least 3 Si—H bonds per molecule are used as cross-linking agent. In addition, organohydrogen polysiloxanes with 2 Si—H bonds per molecule can be used as a so-called chain extenders for influencing the curing behavior and the elasticity behavior.

Alkylhydrogen polysiloxanes can also be used as an alternative to using VQM siloxanes, also benefiting hardness without a large loss in flexibility of the polymer. Thus, for a cross-linking of, for instance, α, ω-divinyl terminated polydimethylsiloxanes, the tetrakis(dimethylsiloxy) silane can be used as multi-functional cross-linking agent. This cross-linking agent is a defined molecule, in contrast to conventionally used alkylhydrogen polysiloxanes which are present in the form of oligomeric mixtures.

The organohydrogen polysiloxanes preferably have two to three Si—H bonds per molecule. In this regards, terminal bonds are preferred, they can however, also be present additionally, or exclusively, in the middle of the chain. Organohydrogen polysiloxanes, the Si—H bonds of which lie in the middle of the chain, are preferred to be relatively short.

The use of organohydrogen polysiloxanes with three Si—H bonds per molecule is particularly preferred.

The quantity of organohydrogen polysiloxane is calculated stoichiometrically to the quantity of the polysiloxanes, comprising polyatomic cross-linkable groups. This generally amounts to 0.5-10% by weight, preferably 0.5-6% by weight and particularly preferably 0.5-2.5% by weight relative to the overall composition of the putty.

For c.)

The catalysis for the reaction of a polydimethysiloxane, comprising polyatomic cross-linkable groups, preferably unsaturated cross-linkable groups, with a polydimethylsiloxane, comprising Si—H functionalities, proceeds involving metal complexes, wherein the Si—H groups can be added to C—C double bonds and C—C triple bonds and also to heteroatom multiple bonds. Suitable catalysts are Pt, Pd, Rh, Ni, Os or Co. Preferably, the metals are used in complexed form. Platinum as a Pt(0) complex with vinyl siloxane ligands is particularly preferably used as a catalyst. The Karstedt catalyst is cited as a particularly preferred catalyst that is formed by reduction and complexing of the platinum in the reaction of divinyl tetramethyl disiloxane with hexachorplatinic acids. The Karstedt catalyst is a Pt(0) complex that has both bridge forming and chelating divinyl ligands.

The documents U.S. Pat. No. 3,715,334, U.S. Pat. No. 3,775,352 and U.S. Pat. No. 3,814,730 for example, the entire contents of which is incorporated herein by reference, describe other suitable and preferably used platinum siloxane complexes that accelerate the addition curing.

The platinum catalyst is used in quantities in the range of 0.0002 to 0.04% by weight, preferably in the range of 10 to 100 ppm by weight and particularly preferably in the range of 15 to 50 ppm by weight, each calculated as elementary platinum, with respect to the total weight of all components of the dental mass.

In many cases, it is expedient to use a plurality of catalysts.

For d.)

The putty mass according to the invention contains further fillers because unfilled silicones are often still too elastic after hardening, and still have unsuitable properties for use as an impression material. Fillers are used in order to adjust and optimize to the desired physical conditions.

The preferred fillers are fillers such as cristobalite, silicate, montmorillonite, bentonite, metal oxide powder, for instance aluminum oxide or zinc oxide, and the mixed oxides thereof, titanium dioxide, magnesium oxide, gypsum, inorganic salt, such as sulfate, carbonate and glass. Further preferred fillers are crystalline silicon dioxide, such as pulverized quartz or diatomaceous earth. Also included in the list of preferred fillers are nanoscaled silicic acids that are present in the form of non-aggregated and non-agglomerated particles, and that can be produced according to the sol-gel process.

The fillers can be surface-treated and are preferably made hydrophobic, for example by treating the surface thereof with organosilanes.

The fillers are selected so that the resulting cured mold has a Shore A hardness, determined according to DIN 53505, of 45 to 85, preferably in the range of 60 to 80.

The fillers can be incorporated in one and/or the other component of the two-component mass. Preferably, the two components are added in similar quantities.

In general, the fillers are used in quantities of 50-90% by weight, preferably 55-80% by weight and particularly preferably 60-70% by weight relative to the total weight of the putty mass.

For e.)

Further, according to the invention, release agents, or respectively plasticizers, are used in the composition of the putty mass. The terms plasticizer and release agent are used interchangeably. The combination of paraffin and alkyl-substituted polydimethylsiloxanes in the dental putty mass is novel. It was surprising to discover that with the addition of a combination of these substances a putty mass can be formulated that has no tacky characteristics and does not release, or respectively sweat, any substances over the entire course of the life cycle thereof, starting from the production of the two pastes, the storage of the pastes, the course of hardening up to the hardened polymer. The mixability of these non-tacky, kneadable and stable pastes is so good that they can be mixed by machine.

Paraffin denotes a mixture of linear and branched saturated hydrocarbons.

Preferred paraffins are mixtures of liquid and solid hydrocarbons. The solid phase can be composed of crystalline and microcrystalline components. The paraffin is preferably composed of a mixture of 60 to 70% of a liquid phase of n-paraffin and isoparaffin and a solid phase composed of crystalline components (10 to 20% n-paraffins) and microcrystalline components (isoparaffins). The paraffin Vaseline® (also called "petrolatum") is particularly preferred.

The petrolatum suited for use in the present invention comprises every degree of white or yellow petrolatum. In general, petrolatum of any viscosity or degree of consistency known in the prior art can be used in this invention. The present invention relates to variants, in which petrolatum is replaced to some extent by a mixture of hydrocarbon materials that can be formulated to emulate petrolatum in appearance and consistency. Such a combination can be formed, for example by melting mineral oil in different portions with substances such as microcrystalline wax, paraffin wax and the like.

Preferred alkyl-substituted polydimethylsiloxanes have at least 8, preferably 16, and particularly preferably at least 18 C atoms in the alkyl chains thereof. The alkyl chain can be linear or branched. Alternatively, polydimethylsiloxanes can also be used in which the linear or branched alkyl chain is completely or partially halogenated, preferably fluorinated.

The length of the side chain amounts to a maximum of 30 C atoms, preferably a maximum of 23 C atoms.

As release agents, a combination of 2-8% by weight, preferably 2-5% by weight, and particularly preferably 2-4% by weight, of at least one alkyl-substituted polydimethylsiloxane is preferably used, with 1-9% by weight paraffin, preferably 2-8% by weight and particularly preferably 3-7% by weight, relative to the total weight of the putty mass.

The advantageous embodiment of the invention with features a.) to e.) additionally has features f.) and/or g.).

For f.)

A particularly preferred embodiment of the mold mass according to the invention has additional components according to feature f).

The reaction between the two components occurs at the ambient temperature (particularly in the mouth of the patient), and is concluded within a few minutes. Therefore in many cases it is necessary to use a retarding agent, also called an inhibitor, in order to control the reaction. Generally, the retarding component comprises any unsaturated substances with low molecular weight that can be used at the beginning of the polymerization in order to delay hardening. Examples of such inhibitors are described in the documents U.S. Pat. No. 3,933,880, U.S. Pat. No. 3,445,420 and U.S. Pat. No. 3,989,667, the entire contents of which is incorporated herein by reference. Examples for this are acetylenic unsaturated alcohols such as 3-methyl-1-butin-3-ol, 1-ethinylcyclohexan-1-ol or 3-methyl-1-pentin-1-ol. They can be used alone or in combination. Compounds based on vinyl siloxane, such as 1,1,3,3-tetramethyl-1,3-divinyldisiloxane and/or oligo- and disiloxanes containing vinyl groups can also be used.

Further types of retarders are compounds that have two or more double bonds, and that via abstraction of an allyl H atom can preferably form a delocalized electron system that extends beyond 5 C atoms. Such compounds can be selected from the group composed of α-terpinenes, β-terpinenes, γ-terpinenes, α-phellandrenes, β-phellandrenes and terpinolenes. Substances that have an exo-double bond are preferably selected.

The preferably used quantity of the inhibitor component is determined primarily based on the type of inhibitor used, so that no generally valid ranges can be specified. If 1,3-divinyltetramethyldisiloxane is used, for example, then at least 0.05 to 0.15% by weight must be added relative to the total mass. If an ethinyl unsaturated alcohol is used, then the quantities 0.0001-0.001% by weight, preferably 0.0005-0.007% by weight and particularly preferably 0.0009-0.002% by weight relative to the total weight of the putty mass are sufficient.

Therefore, ethinyl unsaturated alcohols are particularly preferably used inhibitors.

In the course of cross-linking the polysiloxane system, hydrogen may be released. For this reason, a metal, preferably present in a finely distributed form, is added to the compositions according to the invention. The metal used is preferably platinum or palladium. The metal can also be isolated from a salt. Platinum is used in a quantity of 1 to 1000 ppm, preferably 1 to 500 ppm, and particularly preferably 10 to 50 ppm.

Water absorbing inorganic solids, such as anhydrous calcium sulfate, calcium chloride or similar compounds, or water adsorbing compounds such as zeolite, molecular sieves or similar substances can be added as stabilizers to the composition according to the invention. The quantity of the hydrophilic substance is between 0.1 to 5% by weight, preferably between 0.25-4% by weight, and particularly preferably between 0.5-2% by weight. The stabilizer is not included in d.).

The rheologic properties of the putty mass can be specifically modified by the selective use of plastic powders and/or ultra-high molecular weight siloxanes as rheology modifiers, so that the effects of the above named release agents are further supported, and thereby machine mixing and distribution of the material during use are facilitated. In-house tests have shown that materials even without the fillers named below that have a non-reinforcing effect, can still be processed well by machine, however a higher than usual molding speed is possible with the use of same. This finding was also surprising. The quantity of the rheology modifier is in the range between 1 to 50% by weight, preferably 1 to 20% by weight, and particularly preferably 1 to 10% by weight. Besides organic polymers and high to ultra-high molecular weight siloxanes, the viscosity of which is located in the limit range between high viscosity and already fixed, pyrogenic silicic acids, or respectively kieselguhr, can also be used. Even if the rheology modifier is a solid material, is not included in feature d.) of claim 1.

Solids composed of silicone resins that are soluble in the silicone polymer can also be considered as rheology modifiers.

For g.)

According to a further embodiment, the putty mass according to the invention has further, additional components according to feature g).

Accordingly, the putty composition according to the invention can contain dyes, such as pigments, wetting agents (surface active means) such as tenside, antioxidants and medical and/or pharmaceutical active agents.

The base and catalyst pastes are present in a volume ratio range from 1:1 to 10:1.

The masses according to the invention can be mixed by hand. For this case, the two pastes are preferably present in a volume ratio of 1:1. For the hand mixable variant, the mass is removed from the storage containers thereof (plastic tubs, for example) using metering spoons, mixed by hand, and then in the mixed state, placed into an impression tray. Using the tray, a mold is made of the relevant dental situation in the patient's mouth, either according to the correction impression method, or according to the double mix technique. After curing and removing the mold from the patient's mouth, the mold can then be cut, trimmed or otherwise processed.

The masses according to the invention can also be produced using conventional motor-driven automatic mixing devices, and then used. In such cases, the volume ratio of the base paste and catalyst paste lies a range of 1:1 to 10:1, preferably in a range of 4:1 to 6:1, and particularly preferably 5:1.

The novel two-component dental elastomeric putty material, having high viscosity, dimensional stability and storage durability, based on addition curing silicones, wherein one component comprises a polymerization catalyst, thus contains in the overall composition
  a.) at least one polydimethylsiloxane comprising polyatomic cross-linkable groups, preferably unsaturated cross-linkable groups,
  b.) at least one polyaklysiloxane with Si—H functionalities,
  c.) at least one catalyst for the reaction of a polydimethysiloxane, comprising polyatomic cross-linkable groups, with a polydimethylsiloxane comprising Si—H functionalities,
  d.) one or more fillers,
  e.) a combination of release agents, comprising
    i. at least one alkyl-substituted polydimethylsiloxane, in which the alkyl chain is linear or branched, and/or at least one polydimethylsiloxane, in which the alkyl chain is linear or branched, and partially or completely halogenated, preferably fluorinated, and
    ii. at least one paraffin.
  f.) optionally at least one or more additional components, such as
    i. retarding agents,
    ii. water adsorption means, that are not a component of d.)
    iii. hydrogen adsorption means,
    iv. rheology modifiers, that are not a component of d.) and
  g.) optionally further additives, such as wetting agents, and/or antioxidants and/or dyes, and/or medical and/or pharmaceutical active agents.

Thus, a preferred total composition according to the invention contains:
  a.) at least one polysiloxane comprising (possibly substituted) alkenyl groups, particularly vinyl groups or allyl groups,
  b.) at least one organohydrogen polysiloxane with two to three Si—H bonds per molecule,
  c.) at least one platinum catalyst for the reaction of a polydimethysiloxane, comprising vinyl groups, with a polydimethylsiloxane comprising Si—H functionalities,
  d.) one or more fillers,
  e.) a combination of plasticizers, comprising
    i. at least an alkyl-substituted polydimethylsiloxane, in which the alkyl chain is linear or branched, and/or at least a polydimethylsiloxane, in which the alkyl chain is linear or branched, and partially or completely halogenated, preferably fluorinated, and
    ii. at least one paraffin,
  f.) optional additional components, such as
    i. at least one retarding agent selected from the group of the cycloalkanols and short chain siloxanes, wherein both groups comprise unsaturated side chains, and/or
    ii. at least one water absorption means, such as zeolite or hydrophilic salts, that are not included in d.) and/or
    iii. at least one hydrogen-absorbing metal and/or
    iv. at least one rheology modifier from the group of plastic powders, ultra-high molecular weight siloxanes and pyrogenic silicic acids, with the stipulation that the rheology modifiers are not included in d.), and
  g.) optionally further additives, such as wetting agents, and/or antioxidants and/or dyes, and/or medical and/or pharmaceutical active agents.

Thus, a particularly preferred total composition according to the invention contains:
  a.) at least one linear polysiloxane comprising terminal vinyl groups with a viscosity in the range of 1,000 mPa·s to 20,000 mPa·s, and at least one further linear polysiloxane comprising terminal vinyl groups with a viscosity in the range of 55,000 mPa·s to 120,000 mPa·s,
  b.) at least one organohydrogen polysiloxane with at least three Si—H bonds, c.) at least one Karstedt catalyst for the reaction of a polydimethysiloxane, comprising vinyl groups, with a polydimethylsiloxane comprising Si—H functionalities, d.) one or more fillers, e.) a combination of plasticizers, comprising
   i. at least an alkyl-substituted polydimethylsiloxane, in which the alkyl chain is linear or branched, and/or at least a polydimethylsiloxane, in which the alkyl chain is linear or branched, and partially or completely halogenated, preferably fluorinated, and
   ii. at least one paraffin in the form of Vaseline, f.) additional components, such as
   i. at least ethinylcyclohexanol as a retarding agent and/or
   ii. at least one zeolite as a water absorbing means, that is not included in d.) and/or
   iii. at least one finely distributed, non-complexed platinum as a hydrogen absorbing metal and/or
   iv. at least plastic powder and ultra-high molecular weight siloxane as a rheology modifier, with the stipulation that the rheology modifier is not included in d.), and g.) optionally further additives, such as wetting agents, and/or antioxidants and/or dyes, and/or medical and/or pharmaceutical active agents.

Thus, a particularly preferred total composition according to the invention contains:

a.) 1-40% by weight, preferably 5-30% by weight, particularly preferably 10-25% by weight of a linear polysiloxane comprising terminal vinyl groups with a viscosity in the range of 1,000 mPa·s to 20,000 mPa·s, and at least one further linear polysiloxane comprising terminal vinyl groups with a viscosity in the range of 55,000 mPa·s to 120,000 mPa·s.

b.) 0.5-10% by weight, preferably 0.5-6% by weight, particularly preferably 0.5-2.5% by weight of at least one organohydrogen polysiloxane with at least three Si—H bonds, c.) 0.0002 to 0.04% by weight, preferably 10 to 100 ppm by weight and particularly preferably 15 to 50 ppm by weight, of at least one Karstedt catalyst for the reaction of a polydimethysiloxane, comprising vinyl groups with a polydimethylsiloxane comprising Si—H functionalities, d.) 50-90% by weight, preferably 55-80% by weight and particularly preferably 60-70% by weight of one or more fillers e.) a combination of plasticizers, comprising
   i. 2-8% by weight, preferably 2-5% by weight and particularly preferably 2-4% by weight of at least one alkyl-substituted polydimethylsiloxane in which the alkyl chain is linear or branched, and/or at least one polydimethylsiloxane, in which the alkyl chain is linear or branched and partially or completely halogenated, preferably fluorinated, and
   ii. 1-9% by weight, preferably 2-8% by weight, particularly preferably 3-7% by weight of at least one liquid paraffin in the form of Vaseline, f.) additional components, such as
   i. 0.0001-0.001% by weight, preferably 0.0005-0.007% by weight, and particularly preferably 0.0009-0.002% by weight of at least one ethinylcyclohexanol as a retarding agent, and/or
   ii. 0.1-5% by weight, preferably 0.25-4% by weight, and particularly preferably 0.5-2% by weight of at least one zeolite as a water absorbing means, that is not included in d.), and/or
   iii. 1 to 1000 ppm, preferably 1 to 500 ppm, and particularly preferably 10 to 50 ppm of at least a finely distributed, non-complexed platinum as a hydrogen absorbing metal, and/or
   iv. 1 to 50% by weight, preferably 1 to 20% by weight, and particularly preferably 1 to 10% by weight of at least one plastic powder and an ultra-high molecular weight siloxane as a rheology modifier, with the stipulation that the rheology modifier is not included in d.) and g.) optionally further additives, such as wetting agents, and/or antioxidants and/or dyes, and/or medical and/or pharmaceutical active agents.

It was surprising that the dental compositions, as specified above, satisfy all requirements for a putty mass as specified in the framework of the present invention.

The present invention also comprises molds that are produced using the compositions according to the invention, and method for producing molds according to the invention.

According to a further aspect, the present invention also relates to kits for producing the molds according to the invention, comprising or consisting of compositions according to the invention and application of the molds according to the invention.

An example embodiment of the impression mass according to the invention (Recipe A) was compared to an impression mass according to the prior art (Recipe B).

The recipes are specified in the following and components contained therein are explained.

Recipes for Example Mixtures (portions in weight percent)

A Base

| | |
|---|---|
| Si—H functionalized polydimethylsiloxane (Si—H content: 4.2 mmol/g; Viscosity: 40 mPa · s) | 1.50 |
| Vinyl functionalized polydimethylsiloxane (vinyl content: 0.05 mmol/g; Viscosity: 10000 mPa · s) | 5.7975 |
| Vinyl functionalized polydimethylsiloxane (vinyl content: 0.03 mmol/g; Viscosity: 65000 mPa · s) | 11.90 |
| 1-ethynylcyclohexanol | 0.0025 |
| Stearyl dimethicone | 2.90 |
| Ultra-high molecular weight polydimethylsiloxane (Viscosity: 1000000 mPa · s) | 3.70 |
| Vaseline | 4.50 |
| Polytetrafluorethylene powder | 1.00 |
| Na–A-zeolites (pore width ~4Å) | 1.00 |
| Cristobalite flour (silanized) | 66.70 |
| Pigments | 1.00 |
| Total: | 100.00 |

A Catalyst

| | |
|---|---|
| Karstedt catalyst | 0.004 |
| Vinyl functionalized polydimethylsiloxane (vinyl content: 0.05 mmol/g; Viscosity: 10000 mPa · s) | 7.396 |
| Vinyl functionalized polydimethylsiloxane (vinyl content: 0.03 mmol/g; Viscosity: 65000 mPa · s) | 11.80 |
| Vinyl functionalized polydimethylsiloxane (vinyl content: 1.4 mmol/g; Viscosity: 2200 mPa · s) | 0.80 |
| Stearyl dimethicone | 2.90 |
| Ultra-high molecular weight polydimethylsiloxane (Viscosity: 1000000 mPa · s) | 3.50 |
| Vaseline | 4.90 |

-continued

| | |
|---|---|
| Polytetrafluorethylene powder | 1.00 |
| Na—A-zeolites (pore width ~4Å) | 1.00 |
| Cristobalite flour (silanized) | 66.70 |
| Total: | 100.00 |

B Catalyst

| | |
|---|---|
| Vinyl functionalized polydimethylsiloxane (vinyl content: 0.03 mmol/g; Viscosity: 65000 mPa · s) | 14.97 |
| Vinyl functionalized polydimethylsiloxane (vinyl content: 0.05 mmol/g; Viscosity: 10000 mPa · s) | 6.999 |
| Kieselguhr | 1.81 |
| Cristobalite flour (silanized) | 70.19 |
| Liquid paraffin oil (Viscosity: 160 mPa · s) | 6.02 |
| Karstedt catalyst | 0.0035 |
| Finely distributed platinum | 0.0075 |
| Total: | 100.00 |

B Base

| | |
|---|---|
| Vinyl functionalized polydimethylsiloxane (vinyl content: 0.03 mmol/g; Viscosity: 65000 mPa · s) | 13.93 |
| Si—H functionalized polydimethylsiloxane (Si—H content: 4.7 mmol/g; Viscosity: 40 mPa · s) | 1.12 |
| Vinyl functionalized polydimethylsiloxane (vinyl content: 0.13 mmol/g; Viscosity: 1000 mPa · s) | 5.39 |
| Kieselguhr | 1.95 |
| Liquid paraffin oil (Viscosity: 160 mPa · s) | 6.18 |
| Cristobalite flour (silanized) | 70.30 |
| Si—H functionalized polydimethylsiloxane (Si—H content: 3.4 mmol/g; Viscosity: 3 mPa · s) | 0.53 |
| Pigments | 0.60 |
| Total: | 100.00 |

The pastes in examples A and B were produced by intimate mixing of the components in an Hauschild mixer. The materials were then deaerated in a vacuum for 10 minutes.

The consistencies, according to ISO 4823, amounted to:
Comparison example A: 28 mm
Comparison example B: 23.5 mm Accordingly, the two materials satisfy the necessary criterion (<35 mm) for classification as an impression material with a kneadable putty consistency (type 0).

In order to assess the "non-sweating", described above, the following tests were performed in detail on the impression materials. They were subjectively inspected to detect if drops of fluid were found on the surface of the individual pastes or on the hardened material. In this regard, no sweating could be observed for material A, whereas drops of fluid appeared on the surface of the individual pastes from example B. In addition, "non-sweating", or respectively the "low liquid mass loss" was quantified in that the individual pastes and the hardened material were wiped at defined time intervals using a cellulose cloth, and were each weighed before and after. In this case, possible precipitations were removed by the cloth, and would therefore result in a measurable loss of mass.

Figure 13:
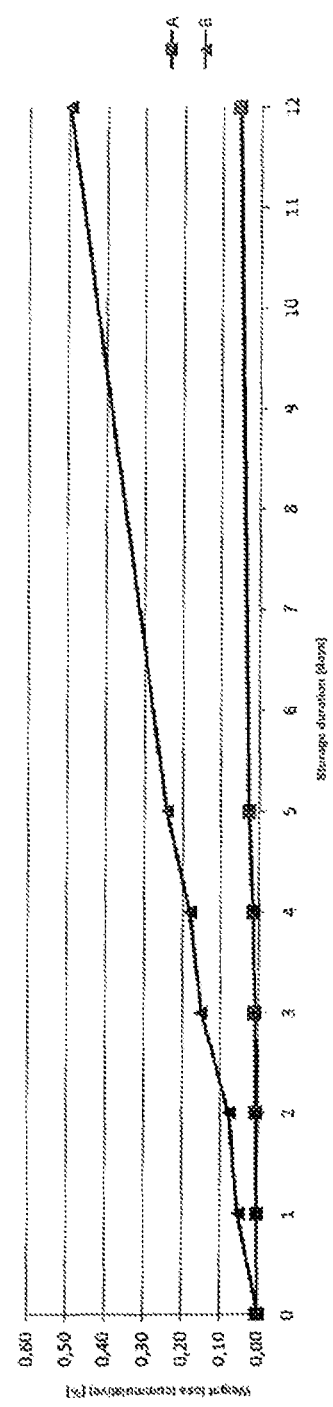
Figure 14:
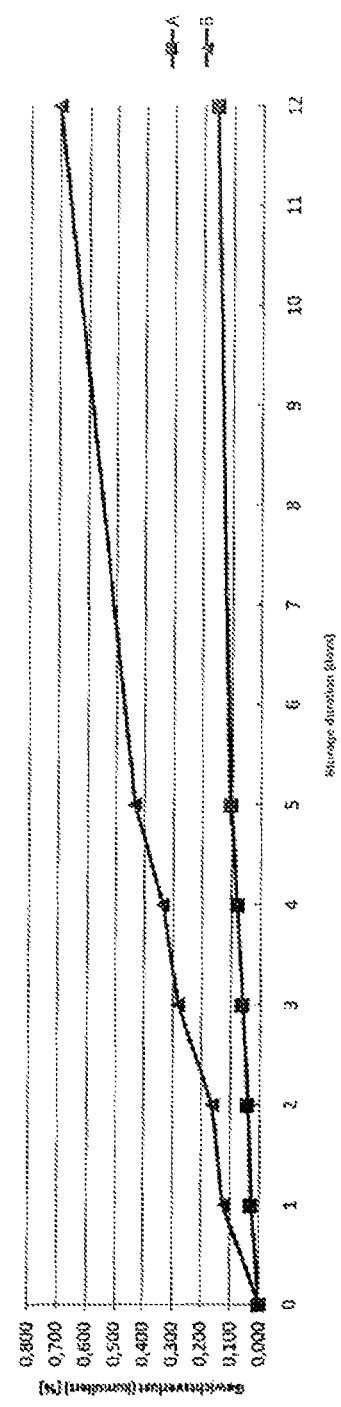

The FIGS. 1 to 14 show the measured results for two different stability tests. The FIGS. 1 to 8 show the cumulative weight loss of the individual pastes caused by sweating at 23, or respectively 37° C. within 140 days (FIGS. 1 to 4 are in absolute value in mg, and FIGS. 5 to 8 are in % by weight). The FIGS. 9 to 14 show the weight loss for the already hardened silicone formulations at 23, 37 and 50° C., likewise in absolute mg (FIGS. 9 to 11) and in percentages (FIGS. 12 to 14). These results are shown for the first five days. The measurements for the sweating behavior were performed as follows:

A sample of approximately 5 g of the respective material (for the hardened example, 2.5 g each of the base paste and catalyst paste were kneaded by hand, intimately mixed, and subsequently hardened at room temperature for 15 minutes) was placed on an acetate film and precisely weighted.

The pastes from examples A and B can be kneaded well by hand, and in the process, are not tacky. This "non-tackiness" is particularly advantageous for using the putty material, as described above.

Subsequently, the samples were stored in a plastic tub at 23° C., or 37° C. After the specified time period, liquid that had accumulated on the surface was dabbed using a cellulose cloth, and then the samples were reweighed.

Based on the definition from the document, U.S. Pat. No. 6,552,104 B1, the entire contents of which is incorporated herein by reference, "non-sweating" means a mass loss of the plasticizer of less than 1% by weight within 24 hours, and a "low fluid mass loss" is a weight reduction of the hardened sample body of less than 0.05% by weight after 12 days at 23° C. The example A according to the invention has a mass loss of 0.04% by weight after this time at 23° C.

The particular advantage of the use of the alkyl-substituted polydimethylsiloxane is significant when one realizes that recipe A contains 1.5% by weight more plasticizer than recipe B, and despite this had a low weight loss due to sweating during storage.

While this invention may be embodied in many different forms, there are described in detail herein a specific preferred embodiment of the invention. This description is an exemplification of the principles of the invention and is not intended to limit the invention to the particular embodiment illustrated.

This completes the description of the preferred and alternate embodiments of the invention. Those skilled in the art may recognize other equivalents to the specific embodiment described herein which equivalents are intended to be encompassed by the claims attached hereto.

What is claimed is:

1. A two-component dental elastomeric impression material with dimensional stability and storage durability based on addition curing silicones, wherein one component comprises a polymerization catalyst, containing:
   a) at least one polydimethylsiloxane comprising polyatomic cross-linkable groups,
   b) at least one polyaklysiloxane with Si—H functionalities,
   c) at least one catalyst for the reaction of a polydimethysiloxane, comprising multiple atom cross-linkable/curable groups, with a polydimethylsiloxane comprising Si—H functionalities
   d) one or more fillers,
   e) a combination of release agents, comprising
      i) at least an alkyl substituted polydimethylsiloxane, in which the alkyl chain is linear or branched, and/or at least a polydimethylsiloxane, in which the alkyl chain is linear or branched, and partially or completely halogenated, wherein the alkyl-substituted polydimethylsiloxane in the alkyl chain thereof, which can be linear or branched, has at least 8 carbon atoms, and has a maximum of 30 carbon atoms, and ii) at least one paraffin;
f) at least one rheology modifier selected from the group consisting of plastic powders and ultra-high molecular weight siloxanes, the rheology modifier not included in d);
wherein the mass in the mixed state has a consistency of less than or equal to 35 mm, determined according to ISO 4823.

2. The two-component dental elastomeric impression material with dimensional stability and storage durability according to claim 1, wherein
a) at least one polysiloxane comprising alkenyl groups,
b) at least one organohydrogen polysiloxane with two to three Si—H bonds per molecule,
c) at least one platinum catalyst for the reaction of a polydimethysiloxane, comprising vinyl groups, with a polydimethylsiloxane comprising Si—H functionalities,
d) one or more fillers,
e) a combination of plasticizers, comprising
   i) at least one alkyl-substituted polydimethylsiloxane, in which the alkyl chain is linear or branched, and/or at least a polydimethylsiloxane, in which the alkyl chain is linear or branched, and partially or completely halogenated, and
   ii) at least one paraffin are contained.

3. The two-component dental elastomeric impression material with dimensional stability and storage durability according to claim 1, wherein
a) at least one linear polysiloxane comprising terminal vinyl groups with a viscosity in the range of 1,000 mPa·s to 20,000 mPa·s, and at least one further linear polysiloxane comprising terminal vinyl groups with a viscosity in the range of 55,000 mPa·s to 120,000 mPa·s,
b) at least one organohydrogen polysiloxane with at least three Si—H bonds, at least one Karstedt catalyst for the reaction of a polydimethysiloxane, comprising vinyl groups, with a polydimethylsiloxane comprising Si—H functionalities,
d) one or more fillers,
e) a combination of plasticizers, comprising
   i) at least one alkyl-substituted polydimethylsiloxane, in which the alkyl chain is linear or branched, and/or at least a polydimethylsiloxane, in which the alkyl chain is linear or branched, and partially or completely halogenated, and
   ii) at least one paraffin in the form of Vaseline are contained.

4. The two-component dental elastomeric impression material with dimensional stability and storage durability according to claim 1, wherein:
a) 1-40% by weight of at least one linear polysiloxane comprising terminal vinyl groups with a viscosity in the range of 1,000 mPa·s to 20,000 mPa·s, and at least one further linear polysiloxane comprising terminal vinyl groups with a viscosity in the range of 55,000 mPa·s to 120,000 mPa·s, wherein the weight ratio of the low viscosity siloxanes to the higher viscosity siloxanes is in the range of 5:1 to 1:5,
b) 0.5-10% by weight of at least one organohydrogen polysiloxane with at least three Si—H bonds,
c) 0.0002 to 0.04% by weight of at least one Karstedt catalyst for the reaction of a polydimethysiloxane, comprising vinyl groups with a polydimethylsiloxane comprising Si—H functionalities,
d) 50-90% by weight of at least one filler e) a combination of plasticizers, comprising
   i) 2-8% by weight of at least one alkyl-substituted polydimethylsiloxane, in which the alkyl chain is linear or branched, and/or at least a polydimethylsiloxane, in which the alkyl chain is linear or branched, and partially or completely halogenated, preferably fluorinated, and
   ii) 1-9% by weight of at least one paraffin in the form of Vaseline, are contained, wherein the weight specifications are relative to the mass of the total composition.

5. The two-component dental elastomeric impression material with dimensional stability and storage durability according to claim 1, wherein the alkyl group of the alkyl-substituted polydimethylsiloxane is linear.

6. The two-component dental elastomeric impression material with dimensional stability and storage durability according to claim 1, wherein the filler is selected from the group of cristobalite, silicate, montmorillonite, bentonite, metal oxide powder, titanium dioxide, magnesium oxide, gypsum, inorganic salts, and glass, crystalline silicon dioxide or diatomaceous earth and nanoscaled silicic acids that are present in the form of non-aggregated and non-agglomerated particles.

7. The two-component dental elastomeric impression material with dimensional stability and storage durability according to claim 6, wherein the filler comprises cristobalite.

8. The two-component dental elastomeric impression material with dimensional stability and storage durability according to claim 1, comprising a base paste and a catalyst paste, wherein the mixture ratio in volume of base paste to catalyst paste in a hand mixable variant is 1:1, and in a machine operated variant is in the range of 1:1 to 10:1.

9. The two-component dental elastomeric impression material with dimensional stability and storage durability according to claim 1, containing
f) at least one of the following components:
   i retarding agents and/or
   ii water absorption substance, that is not a component of d.) and/or
   iii hydrogen absorption substance and/or
   iv rheology modifiers that are not a component of feature d), and/or
g) further additives, such as wetting agents, and/or antioxidants and/or dyes, and/or medical and/or pharmaceutical active agents.

10. The impression material with dimensional stability and storage durability according to claim 1, containing
f) at least one of the following components,
   i at least one retarding agent selected from the group of cycloalkanols and short chain siloxanes, wherein in both cases, the compounds comprise unsaturated side chains, and/or
   ii at least one water absorption substance selected from the group consisting of zeolite, molecular sieves or hydrophilic salts, that are not included in d.) and/or
   iii at least one hydrogen absorbing metal, and/or
   iv at least one rheology modifier selected from the group consisting of pyrogenic silicic acids and kieselguhrs, with the stipulation that the rheology modifier is not included in d), and/or
g) further additives, such as wetting agents, and/or antioxidants and/or dyes, and/or medical and/or pharmaceutical active agents.

11. The impression material with dimensional stability and storage durability according to claim 1, containing f) at least one of the following component,
  i at least ethinylcyclohexanol as a retarding agent and/or
  ii at least one zeolite as a water absorbing substance that is not included in d.), and/or
  iii at least finely distributed non-complexed platinum as a hydrogen absorbing metal, and/or
  iv at least plastic powder and/or ultra-high molecular weight siloxane and/or kieselguhr(s) as rheology modifiers, with the stipulation that the rheology modifiers are not included in feature d), and/or
g) further additives, such as wetting agents, and/or antioxidants and/or dyes, and/or medical and/or pharmaceutical active agents.

12. The impression material with dimensional stability and storage durability according to claim 1, containing
  f) at least one of the following components,
    i 0.0001-0.001% by weight of ethinylcyclohexanol as a retarding agent, and/or
    ii 0.1-5% by weight of at least one zeolite as a water absorbing substance, that is not included in d), and/or
    iii 1 to 1000 ppm of at least a finely distributed, non-complexed platinum as a hydrogen absorbing metal, and/or
    iv 1 to 50% by weight of at least one plastic powder and an ultra-high molecular weight siloxane as a rheology modifier, with the stipulation that the rheology modifier is not included in feature d), and/or
  g) further additives, such as wetting agents, and/or antioxidants and/or dyes, and/or medical and/or pharmaceutical active agents,
  wherein the weight specifications are relative to the mass of the total composition.

13. A dental impression, produced by cross-linking a two-component dental elastomeric impression material with dimensional stability and storage durability according to claim 1.

14. A dental kit comprising either
a two-component dental elastomeric impression material with dimensional stability and storage durability according to claim 1,
one or more mixing tips,
optionally an impression tray or optionally material for producing an individual impression tray,
optionally light, medium, or heavy flowing correction impression material,
or
a two-component dental elastomeric impression material with dimensional stability and storage durability according to claim 1,
one or more metering spoons,
optionally an impression tray or optionally material for producing an individual impression tray,
optionally light, medium, or heavy flowing correction impression material,
optionally a mixing block.

15. A method for producing a dental mold, comprising the steps of:
preparing a two-component dental elastomeric impression material with dimensional stability and storage durability according to claim 1,
preparing a suitable form,
filling the form with the mixed two-component dental elastomeric impression material with dimensional stability and storage durability,
positioning the filled form in the patient's mouth,
hardening the mixed two-component dental elastomeric impression material with dimensional stability and storage durability,
removing the resulting mold from the patient's mouth,
if applicable, cutting, trimming or otherwise processing the resulting mold.

* * * * *